United States Patent [19]
Fields et al.

[11] Patent Number: 5,823,961
[45] Date of Patent: Oct. 20, 1998

[54] CATHETER GUIDEWIRE AND FLUSHING APPARATUS AND METHOD OF INSERTION

[75] Inventors: Charles Bruce Fields, Pittsburg; Gretchen Keser Marchesani, San Jose, both of Calif.

[73] Assignee: HDC Corporation, San Jose, Calif.

[21] Appl. No.: 665,033

[22] Filed: Jun. 5, 1996

Related U.S. Application Data

[63] Continuation-in-part of Ser. No. 327,582, Oct. 24, 1994, abandoned, which is a continuation of Ser. No. 61,481, May 12, 1993, Pat. No. 5,357,961.

[51] Int. Cl.$^6$ .................................................. A61B 5/00
[52] U.S. Cl. ........................... 600/434; 600/585; 604/282
[58] Field of Search ...................... 128/657, 658, 128/772; 604/95, 96, 280–282; 600/433–436, 585

[56] References Cited

U.S. PATENT DOCUMENTS

| | | | |
|---|---|---|---|
| 4,299,226 | 11/1981 | Banka | 128/344 |
| 4,580,573 | 4/1986 | Quinn | 128/657 |
| 4,800,890 | 1/1989 | Cramer | 128/657 |
| 4,850,975 | 7/1989 | Furukawa | 604/170 |
| 4,905,698 | 3/1990 | Strohl, Jr. et al. | 128/737 |
| 4,920,980 | 5/1990 | Jackowski | 128/786 |
| 4,955,862 | 9/1990 | Sepetka | 604/164 |
| 4,988,356 | 1/1991 | Crittenden et al. | 606/192 |
| 5,185,004 | 2/1993 | Lashinski | 604/95 |
| 5,228,452 | 7/1993 | Samson | 128/772 |
| 5,233,979 | 8/1993 | Strickland | 128/207.14 |
| 5,234,407 | 8/1993 | Teirstein et al. | 604/53 |
| 5,236,417 | 8/1993 | Wallis | 604/82 |
| 5,348,536 | 9/1994 | Young et al. | 604/43 |
| 5,357,961 | 10/1994 | Fields et al. | 128/658 |
| 5,372,592 | 12/1994 | Gambale | 604/280 |
| 5,496,292 | 3/1996 | Burnham | 128/657 |

OTHER PUBLICATIONS

Cath–Finder (™) Catheter Tracking System Section 510(k) FDA Application—Sep. 6, 1990.

V–Cath™ With Split Needle Radiopaque, Percutaneous Venous Catheter of Medical Grade Silicon Rubber; HDC Corporation, Aug. 1989.

The advanced PICC just got better, V–Cath™ The right alternative for intermediate and long–term IV therapy with new bloodless flashback chamber and flow–through guidewire; HDC Corporation, Copyright 1991.

510(k) submission K881504 (VEN–A–CATH) HDC Corporation, Mar. 115, 1988.

Intracil and Centracil Catheters line up the best Features for Central Venous IF; Baxter Healthcare Corporation—Copyright 1989.

The Gesco Per–Q–Cath; Gesco International—Copyright 1992.

Photocopy of Intima package label with photograph of actual Intima product with stylet inserted and stylet withdrawn; (Becton Dickinson Cat. No. 3869201, Feb. 1992).

510(k) Notification for Onecath, p. 6, Luther Medical Products, Inc.; Jan. 11, 1993.

510(k) submission K862358 (E–Cath), HDC Corporation, Jun. 23, 1986, and letter to file dated Jul. 1, 1990.

(List continued on next page.)

*Primary Examiner*—Max Hindenburg
*Attorney, Agent, or Firm*—Lyon & Lyon LLP

[57] ABSTRACT

A flushing device comprises a catheter guidewire flushing apparatus comprising a connector having an insertion port, an outlet port and a flushing port and a catheter having rails extending the length thereof. The invention allows a clinician to adjust the length of a catheter, to insert the catheter while flushing to maneuver the catheter through a tortuous blood vessel, and to easily remove the guidewire for safe disposal. The catheter can then be left in place in the blood vessel.

17 Claims, 3 Drawing Sheets

OTHER PUBLICATIONS

Angio–Set®/Intima I.V.Catheter—Suggested Insertion Techniques, Becton Dickinson, 1988.

Intima Advertisement "When it comes to safety in a system, the issue is closed."; Becton Dickinson—Desert Medical, 1990.

S.C. Loughran and M. Borzatta; "Peripherally Inserted Central Catheters: A Report of 2506 Catheter Days" vol. 19 No. 2 Journal of Parenteral and Enteral Nutrition, 1995.

C. Renner, P. P. Knutson and T. Lawson; "Vascular Access in home care: Current Trend" Oct. 1996.

CATHETER GUIDEWIRE AND FLUSHING APPARATUS AND METHOD OF INSERTION

RELATED APPLICATIONS

This application is a continuation-in-part of application Ser. No. 08/327,582, filed Oct. 24, 1994, now abandoned, which is a continuation application of Ser. No. 08/061,481, filed May 12, 1993, now U.S. Pat. No. 5,357,961 (this patent is hereby incorporated by reference).

BACKGROUND OF THE INVENTION

1. Field of the Invention

This invention relates generally to the field of medical devices, and more particularly pertains to the field of catheter guidewire and flushing apparatus.

2. Description of the Prior Art

Peripherally inserted catheters have long been used to access the vascular system because they provide a means of repeated access without causing trauma or pain to the patient. Additionally, when long term vascular access is required (greater then two weeks) a catheter should be used because the alternative, multiple injections, can cause patient discomfort and lead to vein deterioration. When peripheral catheters are installed in a patient's extremity, they are left in the vein and therefore a portion protrudes through the skin for access. These prior art catheters were short (approximately one to one and one-half inches). Their short length results in migration into and out of the vein, an undesired occurrence. This migration provides an opening for infectious agents to enter the vascular system which has led to serious complications. Because of this, peripheral intravascular catheters were usually changed every two to three days. In certain circumstances, they were replaced daily.

Peripherally inserted central catheters, or PICCs, were developed to alleviate some of the problems associated with long-term vascular access using short-term peripheral catheters. The PICC is a much longer catheter designed to be inserted percutaneously such that it reaches deep into the vascular system. The end of the catheter is usually placed in the superior vena cava of the heart to utilize the larger blood volume in that chamber as a diluent for the medication being administered. PICCs are becoming the device of choice for providing access to a patient's vascular system for therapeutic support such as chemotherapy, antibiotic treatment, chemical environment monitoring and intravenous medication.

To place the end of the PICC in the heart, one must be able to navigate the tortuous venous path, which includes many natural blockades (e.g., venous valves). The catheter must be soft and pliable for navigation and comfort. It must also be constructed of biocompatible materials because of the long indwelling period. Catheters having these characteristics are usually manufactured of medical grade polyurethane or silicone rubber, both of which can be made very soft and pliable.

PICC lines made of these soft pliable materials are very difficult and time consuming to install. Their pliant construction allows them to collapse and bend making insertion tedious. Often, it can take up to one hour to insert one catheter, time most clinicians do not have. This also increases the cost of health care.

To ease the difficulty of installation, a flexible metal stylet, or guidewire, is used as a means of stiffening the catheter for insertion. Once the catheter is inserted, the guidewire is removed, leaving the soft, pliable, catheter in the desired position. The two most common guidewire types are of a coiled spring or twist-braided wire construction.

The use of guidewires, however, causes their own problems. A first problem is that friction between the guidewire and catheter inner-wall increases the difficulty of removing the guidewire. The tortuous route the catheter takes in order to reach its final destination causes bends in the catheter guidewire apparatus forcing the guidewire against the inner wall. To reduce this friction, some manufacturers have coated their guidewires with a teflon (PTFE) material, adding some lubricity and thereby reducing the friction between the guidewire and the catheter inner-wall. A second approach to reducing friction is to coat the guidewire with hydrophilic and/or hydrophobic silicone. Such coatings provide lubricating surfaces when they become wet. Both of these methods, which require coating the guidewire, are useful on either the coiled spring or the twist-braided guidewire.

A second problem involved with the use of guidewires is the potential for vessel perforation if the end of the guidewire is forced against the vessel wall. To reduce this danger, coiled spring wires use a soft flexible tip while twist-braided wires have a spherical ball affixed to their ends.

No matter what type of guidewire is used, it is recommended that the catheter be flushed with an aqueous solution before, during, and after catheter insertion. The catheter guidewire apparatus is flushed prior to patient installation in order to check for catheter patency. The catheter is flushed during installation to help maneuver it through the tortuous venous path and to prevent blood from entering the PICC and clotting (an occurrence which makes guidewire removal difficult or impossible). The catheter is flushed after installation in order to facilitate removal of the guidewire. Therefore, there is a need for an apparatus that allows for safe, convenient and economical flushing of catheter guidewire systems before, during and after insertion.

Prior art catheter guidewire apparatus' recommended that the user install the guidewire so that it emerges a little, approximately one-half of one centimeter beyond the end of the catheter. This is for flushing purposes and to provide the user with a portion to hold when removing the guidewire. Traditionally, when flushing a catheter that has a guidewire installed therein, a syringe is connected to the catheter by placing the exposed portion of the guidewire into the tip of the syringe and fastening the syringe to the catheter's fitting. While this method provides a way to supply liquid a interface between the catheter and the guidewire, it has several disadvantages. With this method, the exposed portion of the guidewire is actually inserted inside the syringe's barrel. During flushing, the syringe's plunger naturally moves further into the barrel. A major disadvantage of this system is that the depressing plunger is prone to striking that portion of the guidewire that is within the syringe's barrel. In such a situation, the plunger then may push the guidewire further into the catheter causing the guidewire to actually emerge from the end of the catheter that is deep within a patient. When this occurs, the guidewire, which is now exposed in the patient, can puncture vital organs of the patient such as a lung or a major vein.

This traditional method also does not work well when the catheter is trimmed to length (catheters are made to standard lengths which may be longer than needed to ensure that the tip is installed at the most desirable site). Since the guidewire has a special tip on its end, as discussed above, it is usually not cut and therefore the guidewire must be partially withdrawn prior to trimming. In this situation, there will be considerably more than the normal length of guidewire emerging from the end of the catheter. This excess length of guidewire cannot be inserted in the syringe barrel, thereby preventing the syringe from being placed over the syringe's female luer for flushing. This is a major disadvantage of the prior art.

Some manufacturers suggest that post-catheter shortening flushing when excess guidewire emerges from the female hub can be accomplished by forcing the syringe tip alongside the wire in the end of the catheter, thereby bending the guidewire to the side of the catheter end. A major disadvantage to forcing the syringe in the catheter's end with the guidewire bent away from the syringe's luer is that in such an arrangement there will be no seal between the catheter and the syringe. An incomplete seal will lead to leaks which will prevent adequate flushing. Therefore, since prior art devices are extremely difficult to flush once the catheter has been shortened, guidewire removal, which is a critical requirement of catheter guidewire systems, has been very difficult and a better system and method is needed.

In addition, even after flushing, a guidewire that is coated with either PTFE or hydrophilic and/or hydrophobic silicone can become stuck or difficult to remove. The problem is more common with silicone catheters, since they tend to have be more tacky than other types of catheters. When this occurs, the catheter, which has very little rigidity, and not the guidewire could be pulled out of the patient, causing it to bunch up near the luer hub in an accordion like fashion. This is caused by the surface friction between the guidewire and the catheter wall. Attempting to remove the guidewire after this occurs can lead to minute perforations to the catheter. Thus, if this occurs, it is prudent to remove the entire catheter and install a new catheter. Further, if the friction between the guidewire and the catheter becomes too large, the catheter will be removed from the patient along with the guidewire. If this occurs, the patient's vein must be re-accessed, and a new catheter must be reinstalled in the patient. Finally, when resistance is met during guidewire removal, the guidewire could damage a portion of the catheter located within the patient. If this occurs, the damage will go unknown for a substantial period of time. However, when the internal walls of a catheter are damaged, it is likely that the catheter will rupture at some point, often after approximately two weeks of indwelling.

The present invention overcomes the problems associated with prior art catheter guidewire flushing apparatus. The invention allows the user to flush the catheter before using it to check catheter patency, to flush the catheter during insertion to help maneuver around venous obstructions, to flush the catheter after placement for guidewire removal, to leave the guidewire in place to help visibility when checking placement position radio graphically and to be able to trim a catheter and still maintain a seal between a syringe and the catheter. Further, embodiments of the invention allow for reduced resistance to guidewire removal.

SUMMARY OF THE INVENTION

The present invention overcomes the problems and disadvantages of the prior art through the use of a unique catheter assembly comprising a connector. The preferred connector comprises a three-way connector that comprises an insertion port, a outlet port and a flushing port. The insertion port is preferably collinear with the outlet port and preferably a reclosable septum covers the insertion port.

The assembly of the present invention preferably comprises a peripherally inserted catheter that is connected to the outlet port. A hydrophilic and/or a hydrophobic stylet is slidably disposed such that it extends through the insertion port and outlet port so that the stylet enters the catheter, thereby stiffening it for venous introduction. A plastic handle may be affixed to the distal end of the stylet to provide a means for stylet manipulation and to prevent stylet migration.

To make the removal of the guidewire easier, a plurality of guidewire ribs or rails are disposed within the lumen (or lumens) of the trimmable catheters. The rails extend substantially the entire length of the trimmable catheters. In preferred embodiments, the rails have a triangular cross-section, with isosceles triangles being the most preferred. The rails are preferably spaced such that the guidewire or stylet will only contact a maximum of two rails and such that the guidewire will not contact the troughs between the rails.

A preferred method of using the catheter assembly comprises preparing the assembly for insertion, inserting the catheter and removing the stylet. If desired, the method may include the step of verifying the position of the catheter. The method of preparation comprises the attaching of a syringe filled with a heparin or normal saline solution to the flushing port of the connector, flushing the catheter to check for patency and to remove excess air, adjusting, if desired, the length of the catheter by withdrawing a portion of the stylet from the catheter such that only the desired length of catheter has the stylet within it, and removing the unwanted portion of the catheter.

After any necessary trimming, the catheter is ready for installation in a patient. The method of insertion comprises flushing with the syringe (which is still attached to the flushing port) if undue resistance is felt due to any venous obstructions. This flushing helps to deflect the tip of the catheter to help ease it past the obstruction. The verification step comprises leaving the guidewire in place, radiographically detecting the stylet, and flushing the catheter by simply depressing the syringe's plunger as needed. The method of removal of the guidewire comprises pulling the guidewire handle to move the guidewire out of the catheter. The catheter is flushed if resistance is met when removing the guidewire by depressing the syringe's plunger.

The above and other features of the invention, including various novel details of construction and combination of parts, will now be more particularly described with reference to the accompanying drawings and pointed out in the claims. It will be understood that the particular devices embodying the invention are shown by way of illustration only and not as limitations of the invention. The principles and features of this invention may be employed in various and numerous embodiments without departing from the scope of the invention.

BRIEF DESCRIPTION OF THE DRAWINGS

Reference is made to the accompanying drawings in which are shown illustrative embodiments of aspects of the invention, from which its novel features and advantages will be apparent to those skilled in the art.

BRIEF DESCRIPTION OF THE PREFERRED EMBODIMENT

Figure 1:
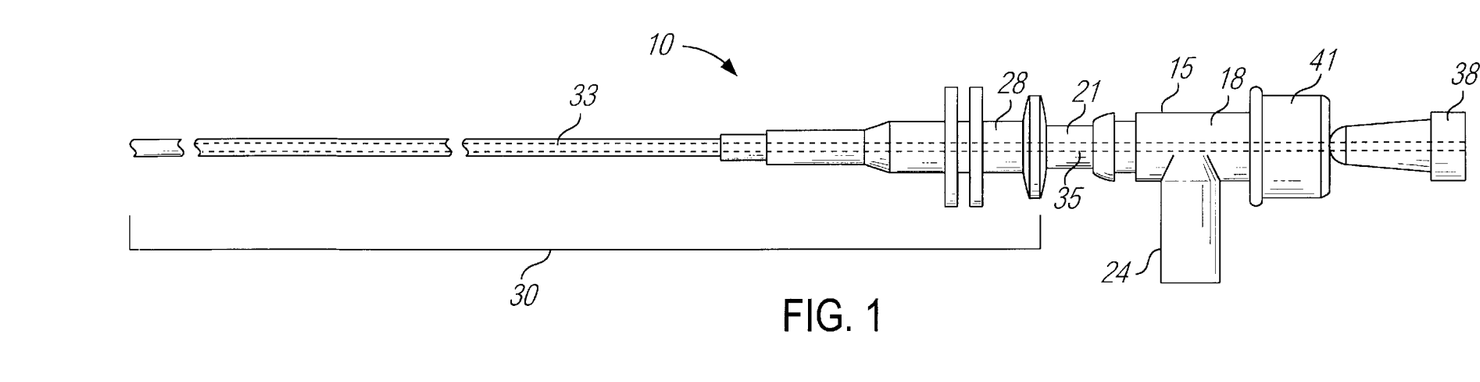
FIG. 1 is a side view of an embodiment of a vascular catheter guidewire flushing apparatus in accordance with the present invention.
Figure 2:
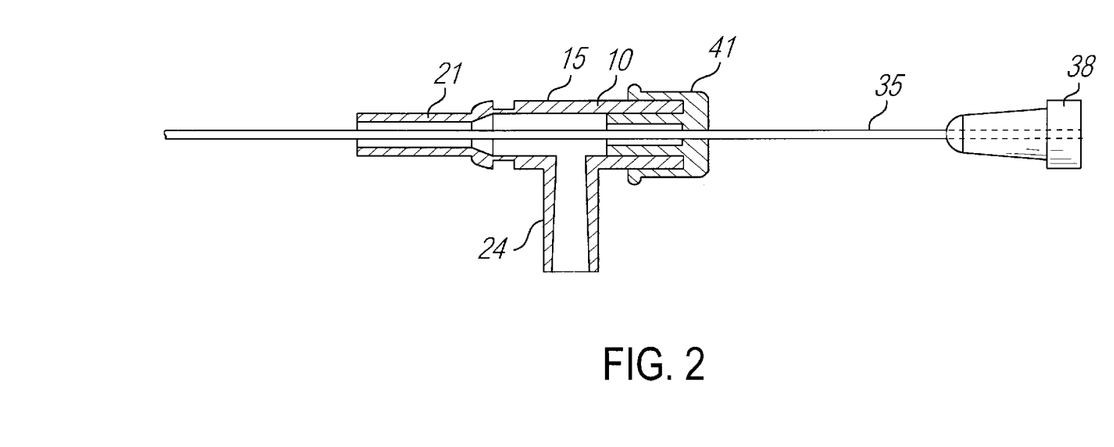
FIG. 2 is an enlarged sectional view of the embodiment of FIG. 1 which shows the catheter guidewire flushing apparatus' three-way connector, septum, and guidewire.

Referring to the drawings, and in particular FIGS. 1 and 2, there is seen an embodiment of a catheter guidewire flushing apparatus 10 of the invention. The guidewire flushing apparatus comprises a three-way connector 15 that comprises an insertion port 18, a outlet port 21 and a flushing port 24. The insertion port 18, outlet port 21 and flushing port 24 are preferably integral to each other and form a cavity.

A peripherally inserted central catheter, or PICC, 30 comprises a female hub 28 and a catheter 33. The female hub 28 and catheter 33 are fastened together to form a continuous and leakless assembly. The catheter 33 can be constructed of any suitable material, such as medical grade polyurethane or silicone rubber. The PICC 30 is connected to the three-way connector 15 by sliding its female hub 28 over the three way connector's 15 outlet port 21. The size of the female hub 28 is selected so that it fits snugly on the outlet port 21 of the three-way connector 15 creating a seal. It will not slide off without application of a substantial force. The outlet port 21 provides communication between the three-way connector 15 and the proximal end of the PICC 30. Disposed on the insertion port 18 is a reclosable septum 41.

In order to make installation of the PICC 30 easier, a guidewire 35 is run through the length of catheter 33. The guidewire 35 stiffens catheter 33, which makes pushing it through a patient's venous system easier. The guidewire 35 preferably comprises a hydrophilically and/or a hydrophobically coated, twist-braided stylet. The guidewire 35 preferably has a handle 38 at its distal end. The handle 38 provides a gripping surface that is larger than the guidewire 35. The large gripping surface makes guidewire handling easier, which simplifies guidewire 35 movement and manipulation, which reduces the amount of time it takes to install the catheter. The handle 38 also acts as a stop to fix the position of the guidewire 35 in relation to the tip of the catheter 33.

The guidewire 35 passes through the reclosable septum 41 disposed on the insertion port 18. The resilient nature of the latex rubber reclosable septum 41 is such that it makes a water tight seal around the guidewire 35. The guidewire 35 then travels through the three-way connector 15 and into the catheter 30. When completely inserted, the guidewire handle 38 will rest against the reclosable septum 41. Initial guidewire 35 length is selected such that when completely inserted, its proximal tip rests approximately one-half to one centimeter from the catheter's 30 proximal tip. This provides additional protection from vein puncture or irritation by the guidewire 35. Once guidewire 35 is completely inserted in PICC 30, the catheter 33 is stiff enough to allow it to move through a vein without being impeded by any venous obstructions.

Once the guidewire 35 is placed through the three-way connector 15, it can slide its full length through the reclosable septum 41. The reclosable septum 41 provides a slight resistance to movement of the guidewire 35. This resistance prevents the guidewire 35 from being moved too quickly through the three-way connector 15 and PICC 30. This is advantageous since moving too quickly can cause patient discomfort and may result in puncturing the vein. Once the wire is removed, the reclosable septum 41 forms a watertight barrier.

Figure 3:
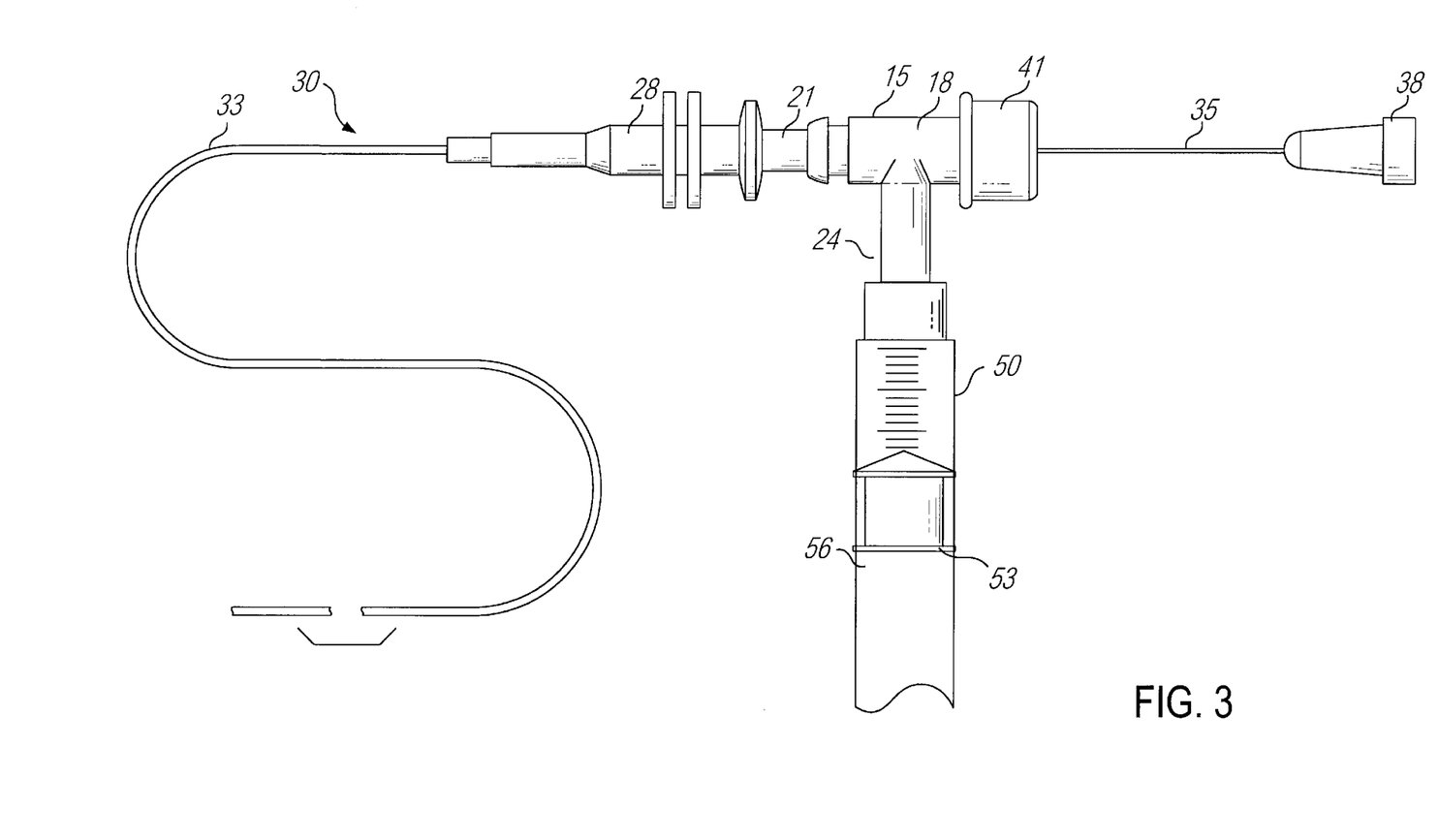
FIG. 3 is a view of catheter trimming technique.

The flushing port 24 provides a means for connecting a syringe 50, as shown in FIG. 3, to the three-way connector 15. The lateral port 24 is preferably disposed perpendicular to the insertion port 18 and outlet port 21. Experimentation has shown that maintaining the lateral port 24 perpendicularly to the insertion port 18 and outlet port 21 provides many advantages. These advantages include insuring that the full force of the injected flushing solution is absorbed by the side wall of the three-way connector 15.

The syringe 50 is filled with flushing solution. Flushing solutions that provide the necessary characteristics include heparin and saline. Once attached to the flushing port 24, the syringe 50 and its contents (the flushing solution) can be left attached until the PICC 30 is installed in its desired position. The normal operation of the syringe 50 will prevent any of the flushing fluid from entering the three-way connector 15 until the syringe's plunger 53 is forced into the syringe's barrel 56.

As discussed, it is possible that even with the vastly improved flushing apparatus 10 disclosed herein that the guidewire 35 could still be difficult to remove, even after flushing and even with guidewires 35 coated with PTFE, hydrophilic or hydrophobic silicone. Thus, a means for reducing the surface friction between the catheter 33 and the guidewire 35 is desired. One way to reduce the surface friction between the catheter 33 and the guidewire 35 would be to apply chemical substrates to either the catheter 33 or the guidewire 35. However, it is desirable that this system not use any chemical substrates because they could cause unacceptable interactions with the medications administered via the catheter 33, they could reduce the safety of the catheter 33 by weakening the catheter, or they could change the performance of the device.

One way to reduce the friction of between the catheter 33 and the guidewire 35 is to reduce the surface area of the catheter 33 that comes into contact with the guidewire 35. In a preferred embodiment of the invention, the guidewire 35 is comprised of a three stranded stainless steel wires that are coiled together in an expanded helix configuration. Thus, the guidewire 35 used in a preferred embodiment of the invention has an irregular surface having high and low points. Use of such a guidewire reduces the surface area of the guidewire 35 that comes into contact with the catheter 33. Further reduction of the surface area of the guidewire 35 is difficult. Thus, in a preferred embodiment of the present invention, the surface area of the inner walls of catheter 33 are arranged such that the surface area of those inner walls are reduced.

Figure 4:
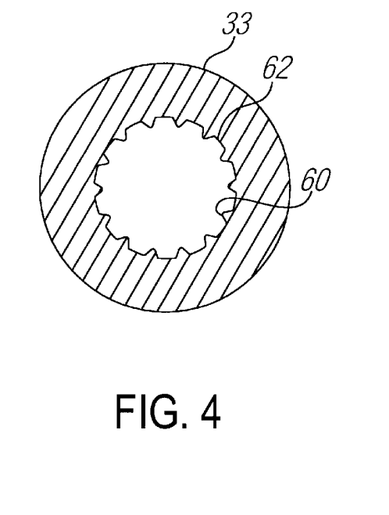
FIG. 4 is an enlarged sectional view of a catheter in accordance with a preferred embodiment of the present invention.

Reference is made to FIG. 4, in which a sectional view of a preferred embodiment of catheter 33 is shown. The lumen of catheter 33 is comprised of a series of raised rails or guidewire ribs 60 and depressed troughs 62 that extend in a substantially linear manner from the proximal to distal end of catheter 33. The raised rails 60 significantly reduce the surface area of the inner wall of catheter 33 that contacts the guidewire 35. When the guidewire 35 is removed, it contacts only rails 60 as it passes through catheter 33. Thus, rails 60 act to lift the guidewire 35 off of the tacky surface of the catheter 35, which significantly reduces the surface friction between the catheter 33 and guidewire 35. Further, troughs 62 act as channels that aid in passing flushing solutions from the three-way connector 15 to the proximal end of catheter 35.

Rails 60 preferably have triangular cross-section. When rails 60 having a triangular cross-section are used, only the apex of the triangle comes into contact with the guidewire 35. This ensures that the guidewire 35 only contacts a very small portion of the catheter's 33 inner wall, which results in a further reduction in the surface friction between the catheter 33 and the guidewire 35. The shape of the triangular cross-section is important, as the apex of the rail 60 will become slightly compressed with the guidewire 35 present. This compression 60 will increase the surface area of the rails 60 that come into contact with the guidewire 35. In a preferred embodiment, rails 60 have an isosceles triangle cross-section. A isosceles triangle cross-section is preferable because the sixty degree angles between the corners inherent in such a structure provide the greatest amount of support for the guidewire, while still maintaining a minimum apex surface area while the guidewire 35 is compressing them.

Figure 5:
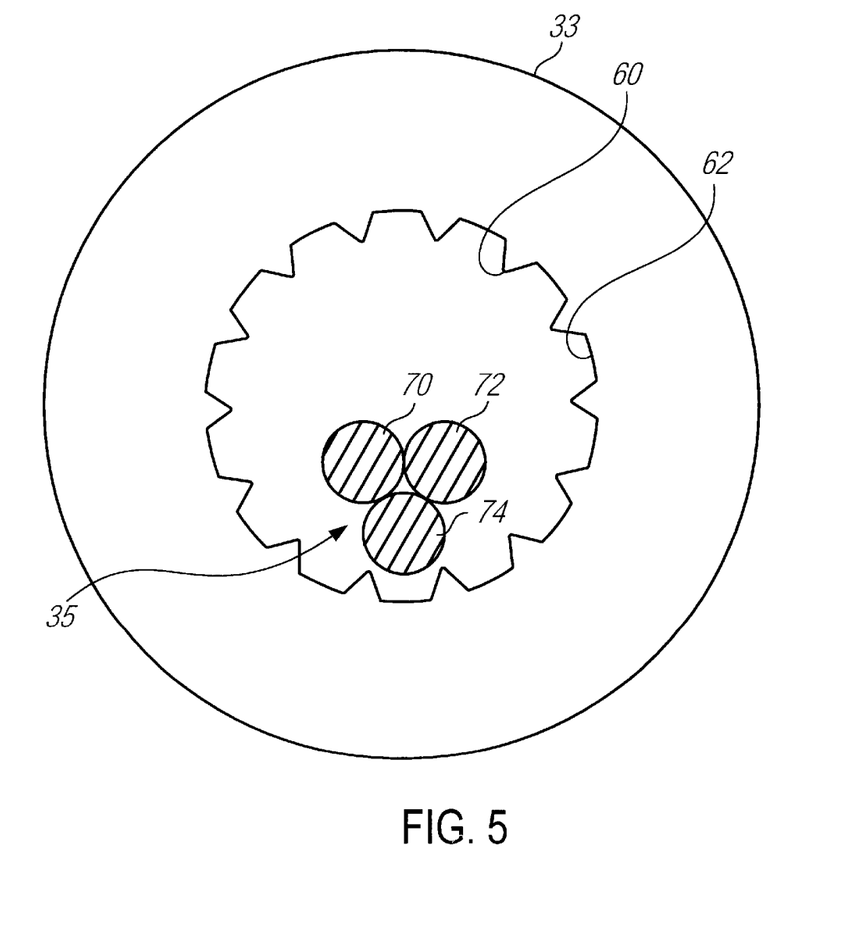
FIG. 5 is an enlarged cross-sectional view of the catheter of FIG. 4 having a guidewire inserted therethrough.

With reference to FIG. 5, a preferred arrangement of rails 60 and troughs 62 will now be discussed. FIG. 5 shows a cross-sectional view of catheter 33 having a guidewire 35 inserted therethrough. The spacing between the rails 60 (which form the troughs 62) is selected such that the guidewire 35 cannot come into contact with the troughs 62 of catheter 33. As discussed, guidewire 35 is comprised of three stranded stainless steel wires 70, 72, 74 that are coiled together in an expanded helix configuration. The rails 60 are arranged such that the guidewire 35 will only contact two rails 60. As shown in FIG. 5, the position of guidewire 35 within catheter 33 is such that, at that particular cross-section, only one strand 74 of the three coiled strands comprising guidewire 35 contacts two rails.

In preferred embodiments of the present invention, a 2.0 French catheter would have ten rails 60, a 3.0 French catheter would have fourteen rails 60, and a 4.0 French catheter would have sixteen rails 60. In each, the rails 60 are, on average, approximately 0.0041 inches apart, with a typical apex-to-apex distance of 0.0044 inches. Each side of the triangle that forms a rail 60 is approximately 0.002 inches, which leads to a rail 60 height of approximately 0.017 inches.

Figure 6:
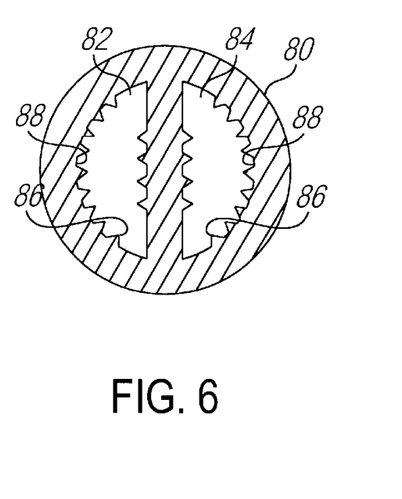
FIG. 6 is an enlarged cross-sectional view of a dual-lumen catheter using the teachings of the present invention.

With reference to FIG. 6, an enlarged cross-sectional view of a dual-lumen catheter 80 using the teachings of the present invention is shown. Catheter 80 comprises first lumen 82 and second lumen 84. Each lumen 82, 84 of catheter 80 is comprised of a series of raised rails 86 and depressed troughs 88 that extend in a substantially linear manner from the proximal to distal end of catheter 80. As in the single lumen catheter 33, when a guidewire such as guidewire 35 is removed, it contacts only rails 86 as it passes through catheter 80. Thus, rails 86 act to lift the guidewire off of the tacky surface of the catheter 80, which significantly reduces the surface friction between the catheter 80 and the guidewire.

The shape, spacing and size of the rails 86 and troughs 88 of the dual lumen catheter 80 are similar to the rails 60 and troughs 62 of the single lumen catheter. Thus, rails 86 preferably have triangular cross-section. A preferred cross-sectional shape of rails 86 is that of an isosceles triangle. The rails 86 are, on average, approximately 0.0041 inches apart, with a typical apex-to-apex distance of 0.0044 inches. Each side of the triangular cross-section that forms a rail 86 is approximately 0.002 inches, which leads to a rail 86 height of approximately 0.017 inches.

With reference to FIG. 3, the method of installing a PICC 30 in a patient will be discussed. In this discussion, the adjustability advantages of the invention will be described.

Prior to installation, the catheter guidewire flushing apparatus 10 must be prepared. The first step in preparing for installation is the flushing of the catheter guidewire flushing apparatus 10. The manner in which the syringe 50 is used to flush the catheter guidewire apparatus 10 has been described above. Flushing prior to installation allows the user to check for patency. The user will know that the PICC 30 has been successfully flushed when drops of flushing solution begin to emerge from the catheter 33 tip.

The next preparation step is to determine how long the PICC 30 needs to be in order for its tip to reach the desired location within the patient. In order to determine this length, the user measures the distance between the insertion site and the desired tip location. If the length necessary for proper catheter 33 tip location is shorter than the length of the catheter 33, the catheter 33 of the PICC 30 must be trimmed to the proper length.

The method of trimming the PICC 30 will now be discussed. It is noted that prior to trimming, the guidewire 35 is placed in the PICC 30 such that the guidewire's 35 handle 38 rests against the reclosable septum 41. The first step in trimming the catheter 33 is to withdraw the guidewire 35 through the reclosable septum 41 so that the guidewire 35 is only within the necessary length of the PICC 30. After the proper length of guidewire 35 has been withdrawn, the catheter 33 portion of the PICC 30 can be trimmed using sterile scissors and being careful to avoid cutting the guidewire. Approximately one centimeter of catheter 33 should remain that has no guidewire within it. The resulting catheter guidewire flushing apparatus 10 has a PICC 30 with a catheter 33 of proper length. Because the guidewire 35 has been withdrawn from the PICC 30, the guidewire 35 handle 38 will no longer rest against the reclosable septum 41 and a portion of the guidewire 35 will no longer be within either the three-way connector 15 or the PICC 30. This is clearly shown in FIG. 3.

After trimming the catheter 33, but immediately prior to installation, the catheter guidewire apparatus 10 may be flushed again. Flushing prior to installation allows the user to recheck catheter patency and can remove any residue created during catheter 33 trimming.

As discussed above, traditional catheter guidewire flushing apparatus' were difficult, if not impossible, to flush when excess guidewire emerged from the PICC 30. In the catheter guidewire flushing apparatus 10 of the invention, however, the provision of flushing port 24 allows the catheter guidewire apparatus 10 to be flushed even though the guidewire 35 has been slightly withdrawn from the PICC 30. Thus, even after trimming, the peripherally inserted catheter can be installed in a patient with the flush feature intact.

It may be necessary to flush the catheter guidewire flushing apparatus 10 during insertion to aid in installation. When the PICC 30 is flushed during installation, the flushing solution will act to slightly move the catheter 33, thereby allowing it to move past any venous obstruction. Flushing during installation can also remove any blood that may accumulate inside the lumen of the PICC 30.

Once installed in the patient, the guidewire 35 can be left in the PICC 30 to verify its placement. This verification will take place radiographically. After this verification, if it was desired, the guidewire 35 must be removed from the PICC 30. In order to remove the guidewire 35, the guidewire's 35 handle 38 is pulled. If any resistance is felt, the PICC 30 should be flushed. As discussed above, the flushing solution lubricates the guidewire 35, thereby making removal much easier. The provision of a separate flushing port 24, unlike traditional guidewire flushing apparatus, allows the flushing to take place without any guidewire 35 manipulation, allows for flushing to take place at any time, without having to reattach a syringe containing flushing solution, and avoids the possibility of puncturing a patient's vein or organ.

Having thus described my invention, what I claim as new and desire to secure by letters patent of the United States of America is:

We claim:

1. A catheter assembly comprising:
   a connector, said connector comprising an insertion port and a outlet port, said insertion port collinear with said outlet port;
   a septum covering said insertion port;
   a catheter fastened to said outlet port, said catheter comprising a lumen having a plurality of rails extending from a proximal end to a distal end of said catheter wherein said plurality of rails have a substantially triangular cross-section;
   a guidewire having an irregular surface, said guidewire slidably disposed through said septum and extending through said insertion port and said outlet port so that said guidewire enters said peripherally inserted central catheter, thereby stiffening said peripherally inserted central catheter for venous introduction; and
   means for flushing said peripherally inserted central catheter with a flushing solution, said flushing solution making said hydrophilic coating on said guidewire slippery, thereby allowing said guidewire to be removed from said peripherally inserted central catheter after venous introduction.

2. The catheter guidewire flushing apparatus of claim 1 wherein said guidewire has a hydrophilic coating.

3. The catheter guidewire flushing apparatus of claim 1 wherein said guidewire has a hydrophobic coating.

4. The catheter guidewire flushing apparatus of claim 1 wherein said guidewire has a PTFE coating.

5. The catheter assembly of claim 1 wherein said means for flushing said peripherally inserted central catheter comprises a flushing port, said flushing port having a syringe filled with said flushing solution disposed thereon, said flushing port perpendicularly opposed to said insertion port and said outlet port.

6. The catheter assembly of claim 1 wherein said substantially triangular cross-section forms an isosceles triangle.

7. The catheter assembly of claim 1 wherein said plurality of rails are spaced apart such that said guidewire contacts a maximum of two rails at any one cross-section of said catheter.

8. A catheter guidewire flushing apparatus comprising:
   a three-way connector, said three-way connector comprising an insertion port, an outlet port and a flushing port, said insertion port collinear with said outlet port and said flushing port disposed perpendicular to said insertion port and said outlet port;
   a septum covering said insertion port;
   a catheter attached to said outlet port, said catheter comprising at least one lumen having a plurality of rails extending from a proximal end to a distal end of said catheter, said plurality of rails having a substantially triangular cross-section; and
   a hydrophilic guidewire slidably disposed through said reclosable septum and extending through said insertion port and said outlet port so that said guidewire enters said catheter, said guidewire thereby stiffening said catheter for venous introduction, said guidewire comprising an irregular surface.

9. The catheter assembly of claim 8 further comprising a female hub affixed to said proximal end of said catheter, said female hub removably attached to said outlet port of said three-way connector to form a continuous, leakless and air-tight assembly.

10. The catheter assembly of claim 8 wherein said substantially triangular cross-section forms an isosceles triangle.

11. The catheter assembly of claim 8 wherein said plurality of rails are spaced apart such that said guidewire contacts a maximum of two rails at any one cross-section of said catheter.

12. A catheter apparatus comprising:
   a three-way connector, said three-way connector comprising an insertion port, an outlet port and a flushing port, said insertion port collinear with said outlet port and said flushing port disposed perpendicular to said insertion port and said outlet port;
   a reclosable septum covering said insertion port;
   a catheter adapted for venous access, said catheter comprising a plurality of rails having a triangular cross-section extending from a proximal end of said catheter to a distal end of said catheter;
   a female hub, said female hub affixed to said proximal end of said catheter, said female hub removably attached to said outlet port of said three-way connector to form a continuous, leakless and air-tight assembly; and
   a guidewire predisposed through an opening in said reclosable septum in frictional relationship with said guidewire, said guidewire comprising an irregular surface, said guidewire extending through said insertion port and said outlet port with said guidewire predisposed in said catheter, thereby stiffening said catheter for venous introduction, said guidewire being in contact with a maximum of two of said plurality of rails.

13. A catheter apparatus comprising:
   a connector comprising a removal port, an outlet port and a flushing port each having a central axis, said removal port substantially collinear with said axis of said outlet port, said axis of said flushing port disposed non-parallel to said axis of said insertion port and said axis of said outlet port;
   a catheter assembly comprising a trimmable catheter and a female hub, said preassembled female hub removably connected to said outlet port of said connector forming a substantially fluid tight attachment, said trimmable catheter comprising at least one lumen;
   a plurality of rails disposed in said at least one lumen of said trimmable catheter, said plurality of rails having a substantially triangular cross-section and extending in a substantially linear fashion from a proximal end to a distal end of said trimmable catheter;
   a reclosable septum disposed over said removal port; and
   a stylet disposed through said reclosable septum, said stylet comprising an irregular surface, said stylet extending through said septum, said removal port and said outlet port and into said catheter.

14. The apparatus of claim 13 wherein said stylet contacts a maximum of two rails at any one cross-section of said trimmable catheter.

15. A catheter apparatus comprising:

a connector including a first port, a second port and a third port, said first port substantially collinear with said second port and said third port disposed non-parallel to said first port and said second port;

a catheter adapted for venous access, said catheter comprising a trimmable catheter with a female hub permanently affixed to a proximal end thereof, said female hub removably fastened to said second port of said connector to form a leakless assembly;

a guidewire comprising an irregular surface predisposed through a non-adjustable seal disposed on said first port, said guidewire extending through said seal, said first port and said second port so that the majority of the length of said guidewire resides in said catheter, said non-adjustable seal allowing said guidewire to be withdrawn from said catheter, said guidewire stiffening said catheter for venous introduction;

said guidewire comprising a handle on that portion of said guidewire outside of said connector and catheter; and said trimmable catheter comprising a plurality of guidewire ribs extending substantially the entire length of said trimmable catheter, said guidewire ribs having a substantially triangular cross-section.

16. The apparatus of claim 15 wherein said non-adjustable seal is comprised of an elastic material.

17. A catheter apparatus comprising:

a stylet assembly comprising a stylet and connector comprising a first port, a second port and a third port, said stylet comprising an irregular surface, said first port substantially collinear with said second port and said third port disposed non-parallel to said first port and said second port;

a catheter adapted for vascular access, said catheter comprising a trimmable catheter with a female hub affixed thereto, said female hub removably fastened to said second port of said stylet assembly to form a leakless assembly;

a non-adjustable seal disposed over said first port, said stylet extending through said non-adjustable seal, said first port and said second port so that said stylet resides in said catheter, said non-adjustable seal allowing said stylet to be pulled out of said catheter, said stylet stiffening said peripherally inserted catheter for venous introduction;

a handle disposed on said stylet on that portion of said stylet outside of said stylet assembly; and said trimmable catheter comprising a plurality of rails extending substantially the entire length of said trimmable catheter, said plurality of rails having a substantially triangular cross-section.

* * * * *